(12) United States Patent
Groenendaal et al.

(10) Patent No.: US 7,094,865 B2
(45) Date of Patent: Aug. 22, 2006

(54) THIOPHENES AND POLYMERS DERIVED THEREFROM

(75) Inventors: Lambertus Groenendaal, Sinaai (BE); Frank Louwet, Diepenbeek (BE); Gianni Zotti, Padua (IT)

(73) Assignee: Agfa Gevaert, Mortsel (BE)

( * ) Notice: Subject to any disclaimer, the term of this patent is extended or adjusted under 35 U.S.C. 154(b) by 351 days.

(21) Appl. No.: 10/104,266

(22) Filed: Mar. 22, 2002

(65) Prior Publication Data

US 2003/0055130 A1    Mar. 20, 2003

Related U.S. Application Data

(60) Provisional application No. 60/291,409, filed on May 16, 2001.

(30) Foreign Application Priority Data

Mar. 29, 2001  (EP) .................. 01000094

(51) Int. Cl.
C08G 75/00 (2006.01)
C08G 65/34 (2006.01)
(52) U.S. Cl. ............... 528/373; 528/377; 528/383; 528/425; 528/480; 524/84
(58) Field of Classification Search ............. 528/377, 528/383, 373, 425, 480; 524/84; 427/388.4
See application file for complete search history.

(56) References Cited

U.S. PATENT DOCUMENTS 5,111,327 A    5/1992    Blohm et al.

FOREIGN PATENT DOCUMENTS

| CA | 2343444 | * | 3/2000 |
|---|---|---|---|
| DE | 19841804 | * | 3/2000 |
| EP | 0 339 340 A2 | | 11/1989 |

OTHER PUBLICATIONS

Bidan et al; "Chirality in Regioregular and Soluble Polythiophene: An Internal Probe of Conformational Changes Induced by Minute Solvation Variation" *Advanced Materials*, Weinheim, DE, vol. 8(2), 157-160 (1996).

(Continued)

*Primary Examiner*—Duc Truong
(74) *Attorney, Agent, or Firm*—Leydig, Voit& Mayer, Ltd.

(57) ABSTRACT

A thiophene compound represented by formula (I):

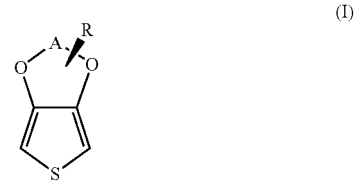

Figure 1:
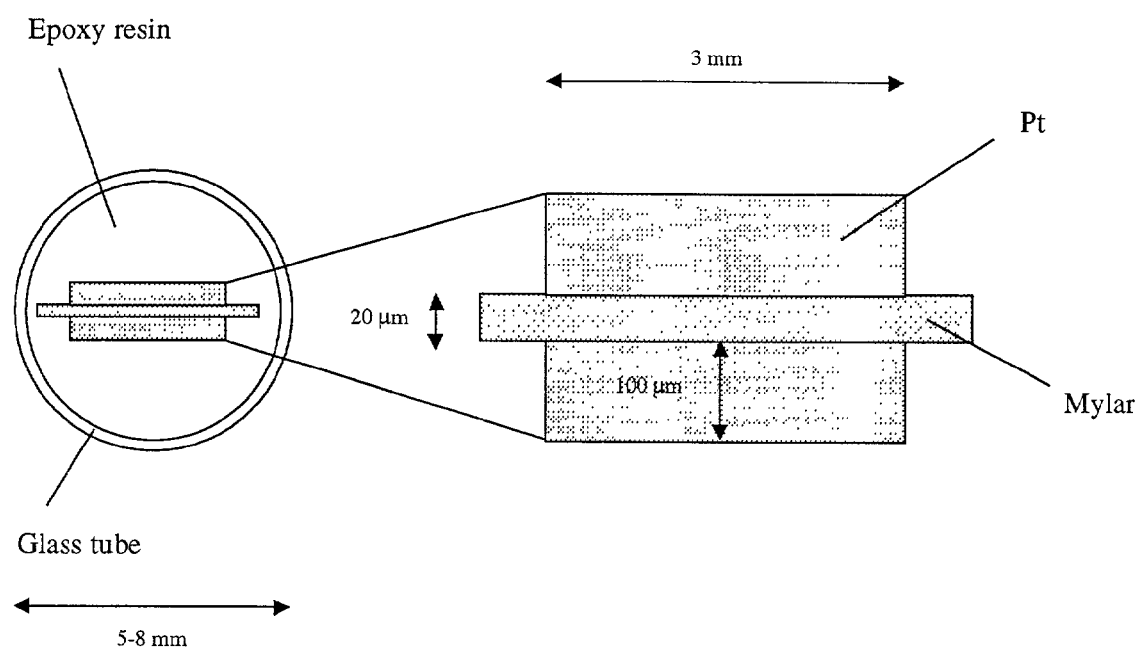

in which:

A represents a C2–C5 alkylene bridge; R represents a stereoselectively substituted, linear or branched C2–C24 alkyl, C3–C18 cycloalkyl, C1–C18 alkoxy or polyethyleneoxide group, optionally substituted with at least one substituent selected from the group consisting of an alcohol, amide, ether, ester or sulfonate group; or an optionally substituted aryl group having at least one chiral center substituted at said C2–C5 alkylene bridge; polymers derived therefrom; a process for polymerizing a thiophene according to formula (I), optionally chemically or electrochemically; and dispersions, pastes and layers containing polymers derived therefrom.

21 Claims, 1 Drawing Sheet

OTHER PUBLICATIONS

Bouman et al; "Chiroptical Properties of Regioregular Chiral Polythiophenes" *Molecular Crystals and Liquid Crystals*, Gordon and Breach, London, vol. 256, 439-448 (1994).

Lemaire et al.; "Enantioselective Chiral Poly(thiophenes)" *Journal of the Chemical Society, Chemical Communications*, Chemical Society. Letchworth GB, 658-661 (1988).

Sankaran et al.; "High-Contrast Electrochromic Polymers From Alkyl-Derivatized Poly (3,4-ethylenedioxythiophenes)" *Macromolecules*, vol. 30, 2582-2588 (1997).

Search Report for EP 01 00 0094 dated Sep. 19, 2001.

* cited by examiner

THIOPHENES AND POLYMERS DERIVED THEREFROM

The application claims the benefit of U.S. Provisional Application No. 60/291,409 filed May 16, 2001.

FIELD OF THE INVENTION

The present invention relates to new thiophene compounds and polythiophenes derived therefrom.

BACKGROUND OF THE INVENTION

Polythiophenes have been studied extensively due to their interesting electrical and/or optical properties. Polythiophenes become electrically conducting upon chemical or electrochemical oxidation or reduction. Their ultimately achievable electrical conductivity is determined by their chemical composition, the stereoregularity of the polymerization of the thiophene monomers in the polythiophene chain and by their π-conjugation lengths. Such stereoregularity problems do not arise when unsubstituted thiophenes or thiophenes substituted in the 3- and 4-positions with identical groups are polymerized.

EP-A 257 573 discloses an intrinsically electrically conductive polymer, wherein through connection in the 2-position and/or the 5-position are coupled to one another, statistically averaged from 60 to 100% by weight structural units, which are derived from at least one monomer of the formula (1):

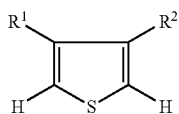

(1)

in which $R^1$ is a C1–C2-alkoxy group or —O(CH$_2$CH$_2$O)$_n$CH$_3$ with n=1 to 4 and $R^2$ is a hydrogen atom, a C1–C12-alkyl group, a C1–C12-alkoxy group or —O(CH$_2$CH$_2$O)$_n$CH$_3$ with n=1 to 4, or $R^1$ and $R^2$ together are —O(CH$_2$)$_m$—CH$_2$— or —O(CH$_2$)$_m$—O— with m=1 to 12, 0 to 40% by weight structural units, which are derived from at least one monomer of the formula (2):

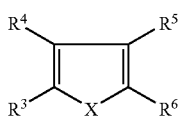

(2)

wherein $R^4$ and $R^5$ are independently of one another a hydrogen atom, a halogen atom, a C1–C12 alkyl group or aryl or together with C-atoms connected to them form an aromatic ring, $R^3$ and $R^6$ independently of one another represent a hydrogen atom or $R^3$ together with $R^4$ and the C-atoms connected to them or $R^5$ together with $R^6$ and the C-atoms connected to them each form an aromatic ring, X represents an oxygen atom, a sulfur atom, a =NH group, a =N-alkyl group or a =N-aryl group, 0 to 40& by weight structural units, which are derived from at least one monomer of formula (3):

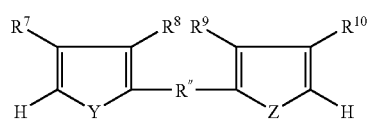

(3)

where $R^7$, $R^8$, $R^9$ and $R^{10}$ independently of one another represent a hydrogen atom, a C1–C12 alkyl group, a C1–C12 alkoxy group or an aryl group, Y and Z independently of one another represent an oxygen atom, a sulfur atom, a =NH group, a =N-alkyl group or a =N-aryl group, $R^{11}$ represents an arylene group, a heteroarylene group or a conjugated system of the formula (CH=CH)$_o$, wherein o is 1, 2 or 3, 0 to 40& by weight structural units, which are derived from at least one monomer of formula (4):

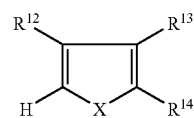

(4)

wherein $R^{12}$ and $R^{13}$ independently of one another represent a hydrogen atom, a halogen atom, a C1–C12 alkyl group, a C1–C12 alkoxy group, a C1–C4 alkylamino group or a C1–C4 acylamino group, $R^{14}$ represents a halogen atom, a C1–C12 alkyl group, a C1–C12 alkoxy group, a C1–C4 alkylamino group or a C1–C4 acylamino group and X has the meaning given above, wherein the polymer in the oxidized form is completely soluble in dipolar aprotic solvents at 25° C. and solutions with a content of at least 0.1 g of the polymer in 100 mL solvent at 25° C. are obtained.

EP-A 339 340 discloses a polythiophene containing structural units of the formula:

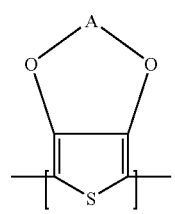

in which A denotes an optionally substituted C1–C4-alkylene radical, its preparation by oxidative polymerization of the corresponding thiophene and exemplifies poly(3,4-ethylene-dioxythiophene), poly[3,4-(1'-methyl)ethylenedioxythiophene], poly[3,4-(1'-n-hexyl)-ethylene-dioxythiophene) and poly[3,4-(1'-n-decyl)ethylenedioxythiophene]. B Sankaran and J. R. Reynolds in 1995 in Polymer Material Science and Engineering, volume 72, pages 319–320 disclosed the synthesis of 3,4-(1'-n-octyl)ethylenedioxythiophene, 3,4-(1'-n-tetradecyl)-ethylenedioxythiophene and their corresponding homopolymers and D. M. Welsh et al. in 1997 in Polymer Preprints, volume 38(2), page 320 disclosed acrylate- and glyme-substituted 3,4-(1'-hydroxymethyl)-ethylenedioxythiophene). S. C. Ng et al. in 1997 in Journal of Materials Science Letters, volume 16, pages 809–811 disclosed the synthesis of 3,4-(1'-allyloxymethyl) ethylenedioxythiophene, 3,4-(1'-glycidoxymethyl-ethylene)

dioxy-thiophene and 3,4-(1'-ω-hydroxyhexyloxymethyl)-ethylenedioxythiophene, 3,4-(2'-allyloxymethyl-propylene)dioxy-thiophene, 3,4-(2'-glycidoxy-methyl)propylenedioxy-thiophene and 3,4-(2'-ω-hydroxyhexyloxy-methyl)propylenedioxy-thiophene and their corresponding homopolymers. O. Stephan, et al. in 1998 in Journal of Electoanalytical Chemistry, volume 443, pages 217–226 disclosed the synthesis of 3,4-(1'-ω-sulfobutyloxymethyl)ethylenedioxythiophene and the corresponding homopolymer. P. Scottland et al. in 1998 in J. Chim. Phys., volume 95, pages 1258–1261 disclosed the synthesis of 3,4-(1'-n-hexyloxymethyl)-ethylenedioxythiophene, 3,4-(1'-n-octyloxymethyl)ethylenedioxy-thiophene, 3,4-(1'-n-decyloxymethyl)ethylenedioxythiophene, 3,4-(1'-n-dodecyloxymethyl)ethylenedioxythiophene, 3,4-(1'-n-tetradecyloxymethyl)ethylenedioxythiophene, 3,4-(1'-n-hexadecyloxymethyl)ethylenedioxythiophene and their corresponding homopolymers. S. Akoudad et al. in 2000 in Electochemistry Communications, volume 2, pages 72–76 disclosed the synthesis of 3,4-(1'-(polyoxyethyleneoxymethyl-ethylene) dioxy-thiophene and the corresponding homopolymer.

D. M. Welsh et al. in 1999 in Polymer Preprints, volume 40(2), page 1206 disclosed the synthesis of 3,4-(2',2'-dimethyl)-propylenedioxythiophene and 3,4-(2',2'-diethyl)propylenedioxythiophene by a transetherification reaction and polymers derived therefrom. L. J. Kloeppner et al. in 1999 in Polymer Preprints, volume 40(2), page 792 also disclosed the synthesis of 3,4-(2',2'-diethyl)propylenedioxythiophene, 3,4-(2',2'-dibutyl)propylene-dioxythiophene and 3,4-(2',2'-dioctyl)propylenedioxythiophene by a transetherification reaction and polymers derived therefrom.

M. Lemaire et al. in 1988 in Journal of the Chemical Society Chemical Communications page 658 disclosed the polymerization of the chiral thiophenes: (S)(+)- and (R)(−)-2-phenylbutyl ether of 3-propylthiophene. M. M. Bouman et al. in 1995 disclosed the polymerization of poly{3-[2-((S)-2-methylbutoxy)ethyl]thiophene}. Furthermore, G. Bidam, S. Guillerez and V. Sorokin in 1996 in Advanced Materials, volume 8, pages 157–160 disclosed the preparation of regioregular poly[3-(S-3',7'-dimethyloctyl)-thiophene]. They showed that if the steric group is far enough removed from the backbone then the conjugation is relatively unaffected and this polymer exhibited large conformational changes induced by minute solvent variation.

B. Groenendaal, G. Zotti and F. Jonas in 2001 in Synthetic Metals, volume 118(1–3), pages 105–109 disclosed the conductivity of electrochemically polymerized 3,4-(1'-methyl)ethylenedioxy-thiophene, 3,4-(1'-n-hexyl-ethylene)-dioxythiophene, 3,4-(1'-n-decyl)ethylene-dioxythiophene and 3,4-(1'-n-tetradecyl)ethylene-dioxythiophene and established that poly(3,4-ethylenedioxy-thiophene)s substituted at the 1'-position with n-alkyl groups with 10 carbon atoms or less exhibited lower electrical conductivities than that of poly(3,4-ethylenedioxythiophene). Poly(3,4-ethylenedioxythiophene) substituted with a n-$C_{14}H_{29}$ group exhibited a 30% increase in electrical conductivity compared with poly (3,4-ethylenedioxy-thiophene) from 650 to 850 S/cm.

A general drawback of conductive polymers which have been prepared and studied up to now, is that their conductivities are still too low for certain applications, their visible light transmittances are insufficiently high and/or they are not processable.

OBJECTS OF THE INVENTION

It is therefore an aspect of the present invention to provide 3,4-alkylenedioxy-thiophenes which upon polymerization provide poly(3,4-alkylenedioxy-thiophene)s, which upon oxidation or reduction exhibit high electrical conductivities, high visible light transmittances and/or good processability.

Further aspects and advantages of the invention will become apparent from the description hereinafter.

SUMMARY OF THE INVENTION

It has been surprisingly found that poly(3,4-ethylenedioxy-thiophene)s in which the ethylene group is stereoselectively substituted with a group, i.e. with a chiral centre at the ethylene bridge, exhibit improved electrical conductivities in the oxidized state compared with polymers produced using a racemic mixture of its enantiomeric monomers. For example in the case of the polymerization of chiral 2-n-decyl-2,3-dihydro-thieno[3,4-b][1,4]dioxine rather than a racemic mixture of the d- and l-forms of 2-hexyl-2,3-dihydro-thieno[3,4-b][1,4]dioxine an increase in electrical conductivity of a factor of 9 was observed using the polymerization and measurement techniques disclosed by Groenendaal et al. in 2001 in Synthetic Metals, volume 118(1–3), on pages 105–109. This electrical conductivity value was also a factor of almost 2.8 higher than that of poly(3,4-ethylenedioxy-thiophene) using the same polymerization and measurement techniques.

A thiophene compound is provided by the present invention represented by formula (I):

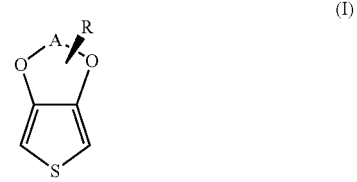

in which:
A represents a C2–C5 alkylene bridge; R represents a stereoselectively substituted, linear or branched C2–C24 alkyl, C3–C18 cycloalkyl, C1–C18 alkoxy or polyethyleneoxide group, optionally substituted with at least one substituent selected from the group consisting of an alcohol, amide, ether, ester or sulfonate group; or an optionally substituted aryl group having at least one chiral centre substituted at said C2–C5 alkylene bridge.

A poly(3,4-alkylenedioxythiophene) is further provided by the present invention derived from the above-mentioned thiophene according to formula (I).

A process is also provided according to the present invention for polymerizing the above-mentioned thiophene.

A dispersion is also provided according to the present invention containing a poly(3,4-alkylenedioxy-thiophene) derived from the above-mentioned thiophene according to formula (I).

A printable paste is also provided according to the present invention containing a poly(3,4-alkylenedioxy-thiophene) derived from the above-mentioned thiophene according to formula (I).

Use of a dispersion containing a poly(3,4-alkylenedioxy-thiophene) derived from the above-mentioned thiophene according to formula (I) for coating an object, such as a glass plate, a plastic foil, paper etc., is also provided by the present invention.

An electroconductive layer is also provided according to the present invention containing a poly(3,4-alkylenedioxy-thiophene) derived from the above-mentioned thiophene according to formula (I).

An antistatic layer is also provided according to the present invention containing a poly(3,4-alkylenedioxythiophene) derived from the above-mentioned thiophene according to formula (I).

DETAILED DESCRIPTION OF THE INVENTION

FIG. 1 is a schematic representation of the three electrode cell used for electrochemically polymerizing the chiral thiophene compounds according to formula (I). Two 100 μm thick and 3 mm wide platinum bands are kept apart with a 20 μm Mylar™ spacer and embedded in epoxy resin in a glass tube 5–8 mm in diameter.

DEFINITIONS

It should be noted that as used in the specification and the appended claims, the singular forms "a" and "an" include plural references unless the context clearly dictates otherwise. Thus, for example, reference to "a thiophene according to formula (I)" includes more than one such thiophene, reference to polymerization of "a thiophene according to formula (I)" includes copolymerization of more than one such thiophene.

The term C1–C5 alkylene group represents oxymethyleneoxy, 1,2-dioxyethylene, 1,3-dioxypropylene, 1,4-dioxybutene and 1,5-dioxypentene groups.

The term alkyl means all variants possible for each number of carbon atoms in the alkyl group i.e. for three carbon atoms: n-propyl and isopropyl; for four carbon atoms: n-butyl, isobutyl and tertiary-butyl; for five carbon atoms: n-pentyl, 1,1-dimethyl-propyl, 2,2-dimethylpropyl and 2-methyl-butyl etc.

A chiral centre is an atom, e.g. a carbon atom, that is attached to four different groups. A molecule containing a chiral centre is not superimposable upon its mirror image and will exhibit chirality, chirality being the handedness of an asymmetric molecule. Such molecules, if isolated in a pure-state, will generally exhibit rotation of polarized light detectable with a polarimeter.

The term racemic mixture of d- and l-compounds means that the compound has an optically active group and the precise mixture of d- and l-enantiomers is determined statistically.

A triflate group is a trifluoromethylsulfonate group.

A mesylate group is a methylsulfonyl group.

A Sharpless epoxidation is an aymmetric epoxidation as described by A. Pfenninger in 1986 in Synthesis on pages 89–116.

The term aqueous for the purposes of the present invention means containing at least 60% by volume of water, preferably at least 80% by volume of water, and optionally containing water-miscible organic solvents such as alcohols e.g. methanol, ethanol, 2-propanol, butanol, iso-amyl alcohol, octanol, cetyl alcohol etc.; glycols e.g. ethylene glycol; glycerine; N-methyl pyrrolidone; methoxypropanol; and ketones e.g. 2-propanone and 2-butanone etc.

Thiophene Compounds According to Formula (I)

According to a first embodiment of the present invention the thiophene compounds of formula (I) have an R group in which R is a C4–C20 alkyl group.

According to a second embodiment of the present invention the thiophene compounds of formula (I) have an R group in which R is a C6–C18 alkyl group.

According to a third embodiment of the present invention the thiophene compounds of formula (I) have an R group in which R is a C6–C14 alkyl group.

According to a fourth embodiment of the present invention the thiophene compounds of formula (I) have an R group in which the group R contains an ether, an ester or an amide substituent, or in which at least one of the substituents is selected from the group consisting of a sulfonate, phosphonate, halogen and hydroxy group.

Thiophene compounds according to formula (I), according to the present invention, can be prepared by known methods such the transetherification reaction disclosed in DE 3804522 and in HOUBEN-WEYL, volume VI/3, part 3, pages 171–173 (1971) using a thiophene derivative such as 3,4-dimethoxythiophene, or the double Williamson reaction as disclosed in 1994 in Electrochimica Acta in volume 39, pages 1345–1347 using a thiophene derivative such as the dimethyl ester of 3,4-dihydroxythiophene-2,5-dicarboxylic acid. Chiral molecules represented by formula (II):

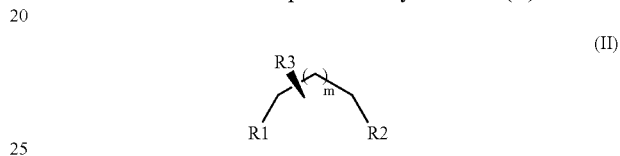

(II)

in which: $R^1$ and $R^2$ independently represent OH, a halogen, a mesylate substituent, a triflate substituent, a tosylate or other sulfonate substituent; $R^3$ represents a steroselectively substituted, linear or branched, optionally substituted C2–C18 alkyl, C3–C18 cycloalkyl, C1–C18 alkoxy or polyethyleneoxide group (optionally with at least one substituent selected from the group consisting of an alcohol, amide, ether, ester and sulfonate group) or an optionally substituted aryl group; and m represents a number from 0 to 3, are reagents for the preparation of the thiophene derivatives represented by formula (I). Chiral molecules according to general formula (II) can be prepared using standard methods known in organic chemistry e.g. asymmetric dihydroxylation or halogenation of olefins e.g. substituted ethene, propene, 1- or 2-butene, 1,2-dimethyl-3-butene-2,3,1-pentene, 1-hexene, 1-octene, 1-decene, asymmetric ring opening of epoxides, asymmetric epoxidation e.g. Sharpless epoxidation followed by dihydroxylation. They can also be separated from racemic mixtures of enantiomers by complexing one enantiomer with a chiral molecule. Several compounds are also commercially available e.g. (S)-(+)-1,2-propandiol and (S)-(+)-1,2-dodecanediol.

Poly(3,4-alkylenedioxythiophene)s Derived from Thiophene Compounds According to Formula (I)

A fifth embodiment of the present invention is a poly(3, 4-alkylenedioxy-thiophene) derived from a thiophene compound according to formula (I).

A sixth embodiment of the present invention is a poly(3, 4-alkylenedioxythiophene) selected from the group consisting of:
poly{chiral 2-hexyl-2,3-dihydro-thieno[3,4-b][1,4]dioxine},
poly{chiral 2-octyl-2,3-dihydro-thieno[3,4-b][1,4]dioxine} and
poly{chiral 2-decyl-2,3-dihydro-thieno [3,4-b][1,4]dioxine}.

A seventh embodiment of the present invention is a poly(3,4-alkylenedioxythiophene) selected from the group consisting of:

poly{chiral 2-hexyl-2,3-dihydro-thieno[3,4-b][1,4]dioxine}, poly{chiral 2-octyl-2,3-dihydro-thieno[3,4-b][1,4]dioxine} and poly{chiral 2-decyl-2,3-dihydro-thieno[3,4-b][1,4]dioxine}, poly{chiral 2-dodecyl-2,3-dihydro-thieno[3,4-b][1,4]dioxine}, poly{chiral 2-tetradecyl-2,3-dihydro-thieno[3,4-b][1,4]dioxine}, poly{chiral 2-hexadecyl-2,3-dihydro-thieno[3,4-b][1,4]dioxine} and poly{chiral 2-octadecyl-2,3-dihydro-thieno[3,4-b][1,4]dioxine}.

An eighth embodiment of the present invention is poly{chiral 2-n-hexyl-2,3-dihydro-thieno[3,4-b][1,4]dioxine}.

A ninth embodiment of the present invention is poly{chiral 2-n-octyl-2,3-dihydro-thieno[3,4-b][1,4]dioxine}.

A tenth embodiment of the present invention is poly{chiral 2-n-decyl-2,3-dihydro-thieno[3,4-b][1,4]dioxine}.

Chemical Polymerization of Thiophene Compounds According to Formula (I)

Thiophene compounds according to formula (I) can be polymerized chemically (oxidatively and reductively). The oxidation agents used for the oxidative polymerisation of pyrrole, such as described for example in Journal of the American Chemical Society, volume 85, pages 454–458 (1963) and J. Polymer Science Part A Polymer Chemistry, volume 26, pages 1287–1294 (1988), can be utilized for the oxidative polymerization of thiophenes. According to a seventh embodiment of the present invention, the inexpensive and easily accessible oxidation agents such as iron(III) salts such as $FeCl_3$, the iron(III) salts of organic acids, e.g. Fe(OTs)$_3$, $H_2O_2$, $K_2Cr_2O_7$, alkali and ammonium persulfates, alkali perborates and potassium permanganate are used in the oxidative polymerization.

Theoretically the oxidative polymerization of thiophenes requires 2.25 equivalents of oxidation agent per mole thiophene of formula (I) [see e.g. J. Polymer Science Part A Polymer Chemistry, volume 26, pages 1287–1294 (1988)]. In practice an excess of 0.1 to 2 equivalents of oxidation agent is used per polymerizable unit. The use of persulfates and iron(III) salts has the great technical advantage that they do not act corrosively and particularly in the case of the thiophene compounds according to formula (I) oxidative polymerization proceeds so slowly that the thiophenes and oxidation agent can be brought together as a solution or paste and applied to the substrate to be treated. After application of the solution or paste the oxidative polymerization can be accelerated by heating the coated substrate.

Reductive polymerization can be carried out using Stille (organotin) and the Suzuki (organoboron) routes as disclosed in 2001 in Tetrahedron Letters, volume 42, pages 155–157 and in 1998 in Macromolecules, volume 31, pages 2047–2056 respectively or with nickel complexes as disclosed in 1999 in Bull. Chem. Soc. Japan, volume 72, page 621 and in 1998 in Advanced Materials, volume 10, pages 93–116.

Thiophene compounds according to formula (I) may also be chemically copolymerized with other polymerizable heterocyclic compounds such as pyrrole.

Electrochemical Polymerization of Thiophene Compounds According to Formula (I)

Thiophene compounds according to formula (I) can be polymerized electrochemically. Electrochemical oxidative polymerization of thiophene compounds according to formula (I) carried out at temperatures from −78° C. to the boiling point of the solvent employed, temperatures between −20° C. and 60° C. is preferred. The reaction time, depending upon the particular thiophene, is generally between a few seconds and several hours. Electrochemical polymerization of thiophene compounds was described in 1994 by Dietrich et al. in Journal Electroanalytical Chemistry, volume 369, pages 87–92.

Inert liquids suitable for use during electrochemical oxidation of thiophene compounds according to formula (I) are: water, alcohols such as methanol and ethanol, ketones such as acetophenone, halogenated hydrocarbons such as methylene chloride, chloroform, tetrachloromethane and fluorohydrocarbons, esters such as ethyl acetate and butyl acetate, aromatic hydrocarbons such as benzene, toluene and xylene, aliphatic hydrocarbons such as pentane, hexane, heptane and cyclohexane, nitriles such as acetonitrile and benzonitrile, sulfoxides such as dimethylsulfoxide, sulfones such as dimethylsulfone, phenylmethylsulfone and sulfolan, liquid aliphatic amides such as methyl acetamide, dimethyl acetamide, dimethyl formamide, pyrrolidone, N-methylpyrrolidone, caprolactam, N-methyl-caprolactam, aliphatic and mixed aliphatic and aromatic ethers such as diethylether and anisole, liquid ureas such as tetramethylurea or N,N-dimethyl-imidazolidinone.

Electrolyte additives for use in the electrochemical polymerization of thiophene compounds according to formula (I) are preferably free acids or the usual conducting salts, which exhibit a certain solubility in the solvent used. Particularly suitable electrolytes are alkali, alkaline earth or optionally alkylated ammonium, phosphonium, sulfonium or oxonium cations in combination with perchlorate, tosylate, tetrafluoroborate or hexafluorophosphonate anions.

The electrolyte additives are used in such quantities, that a current of at least 0.1 mA flows during electrochemical oxidation.

Electrochemical polymerization can be carried out continuously or discontinuously. Known electrode materials are ITO-covered glass, precious metal or steel mesh, carbon-filled polymers, evaporated metal-coated insulator layers and carbon felt.

Current densities during electrochemical oxidation may vary within wide limits. According to an eleventh embodiment of the present invention the current densities in the electroconductive layer is 0.0001 to 100 mA/cm$^2$. According to a twelfth embodiment of the present invention the current density in the electroconductive layer is 0.01 to 40 mA/cm$^2$. At these current densities voltages of ca. 0.1 to 50 V are set up.

Thiophene compounds according to formula (I) may also be electrochemically copolymerized with other polymerizable heterocyclic compounds such as pyrrole.

Dispersion Containing a poly(3,4-alkylenedioxy-thiophene) Derived from a Thiophene According to Formula (I)

According to a first embodiment of the dispersion according to the present invention, the dispersion further contains a polyanion.

According to a second embodiment of the dispersion according to the present invention, the dispersion further contains poly(styrene sulphonic acid).

According to a third embodiment of the dispersion according to the present invention, the dispersion medium is an aqueous dispersion medium.

Polyanion Compound

The polyanion compounds for use in the dispersion according to the present invention are disclosed in EP-A 440 957 and include polymeric carboxylic acids, e.g. polyacrylic acids, polymethacrylic acids, or polymaleic acids and polysulphonic acids, e.g. poly(styrene sulphonic acid). These polycarboxylic acids and polysulphonic acids can also be copolymers of vinylcarboxylic acids and vinylsulphonic acids with other polymerizable monomers, e.g. acrylic acid esters, methacrylic acid esters and styrene.

INDUSTRIAL APPLICATION

Chemically or electrochemically prepared polymers derived from chiral thiophene compounds according to formula (I) exhibit high electrical conductivity together with low absorption of visible light and high absorption to infrared radiation. Therefore layers thereof are highly electrically conducting, highly transparent to visible light and heat shielding. Such polythiophenes can be applied to a wide variety of rigid and flexible substrates, e.g. ceramics, glass and plastics, and are particularly suitable for flexible substrates such as plastic sheeting and the substrates can be substantially bent and deformed without the polythiophene layer losing its electrical conductivity.

Such polythiophenes can therefore be utilized in photovoltaic devices, batteries, capacitors and organic and inorganic electroluminescent devices, in electromagnetic shielding layers, in heat shielding layers, in antistatic coatings for a wide variety of products including photographic film, thermographic recording materials and photothermographic recording materials, in smart windows, in electrochromic devices, in sensors for organic and bio-organic materials, in field effect transistors, in printing plates, in conductive resin adhesives and in free-standing electrically conductive films [see also chapter 10 of the Handbook of Oligo- and Polythiophenes, Edited by D. Fichou, Wiley-VCH, Weinheim (1999)].

The invention is illustrated hereinafter by way of comparative and invention examples. The percentages and ratios given in these examples are by weight unless otherwise indicated. The optical rotation of the chiral compounds was determined for three concentrations in n-hexane with an Optical Activity AA10 multi-wavelength polarimeter at 25° C. using a 5 cm cell with an internal diameter of 5 mm at wavelengths of 365, 436, 540, 578 and 589 nm.

COMPARATIVE EXAMPLE 1

Synthesis of chiral
2-methyl-2,3-dihydro-thieno[3,4-b][1,4]dioxine

A solution of 3,4-dimethoxythiophene (5.18 g), (S)-1,2-propanediol (3.0 g) and p-toluenesulfonic acid monohydrate (100 mg) in toluene (50 ml) was heated at 95° C. during which a continuous stream of nitrogen was passed over the solution. After 30 h the reaction mixture was poured into ethyl acetate, washed with NaHCO$_3$ and the organic phase was concentrated. Subsequent filtration over SiO$_2$ using n-hexane as eluant resulted in pure product (3.90 g). GC-MS: 156 (purity>99%); $^1$H-NMR (CDCl$_3$): δ 6.30 (2×d, 2H), 4.26 (m, 1H), 4.15 (dd, 1H), 3.82 (dd, 1H), 1.35 (d, 3H) ppm; specific rotation [α]=−46° at 25° C. and 436 nm in hexane (c=0.066).

COMPARATIVE EXAMPLE 2

Synthesis of racemic
2-methyl-2,3-dihydro-thieno[3,4-b][1,4]dioxine

Racemic 2-methyl-2,3-dihydro-thieno[3,4-b][1,4]dioxine was synthesized by transetherification of 3,4-dimethoxythiophene with racemic 1,2-propanediol as described in COMPARATIVE EXAMPLE 1. It was characterized by GC-MS and H-NMR-spectroscopy, and exhibited no optical rotation.

INVENTION EXAMPLE 1

Synthesis of chiral
2-n-decyl-2,3-dihydro-thieno[3,4-b][1,4]dioxine

A solution of 3,4-dimethoxythiophene (1.90 g), toluene (30 ml), (S)-1,2-dodecanediol (2.50 g) and p-toluenesulfonic acid monohydrate (100 mg) was heated at 95° C., continuously leading a N$_2$-stream over the solution. After 24 h the reaction mixture was poured into ethyl acetate, washed with NaHCO$_3$ and the organic phase was concentrated. Subsequent filtration over SiO$_2$ using n-hexane/CH$_2$Cl$_2$ (98/2) as eluant resulted in pure product (2.40 g).

$^1$H-NMR (CDCl$_3$): δ 6.29 (s, 2H), 4.15 (dd, 1H), 4.11 (m, 1H), 3.93 (dd, 1H), 1.67–1.20 (18H), 0.88 (t, 3H) ppm; specific rotation [α]=−88° at 25° C. and 436 nm in hexane (c=0.066).

COMPARATIVE EXAMPLE 3

Synthesis of racemic
2-n-decyl-2,3-dihydro-thieno[3,4-b][1,4]dioxine

Racemic 2-n-decyl-2,3-dihydro-thieno[3,4-b][1,4]dioxine was synthesized by transetherification of 3,4-dimethoxythiophene with racemic 1,2-dodecanediol as described in EXAMPLE 1. It was characterized by GC-MS and H-NMR-spectroscopy, and exhibited no optical rotation.

INVENTION EXAMPLE 2

Synthesis of chiral
2-n-hexyl-2,3-dihydro-thieno[3,4-b][1,4]dioxine

Chiral 2-n-hexyl-2,3-dihydro-thieno[3,4-b][1,4]dioxine was synthesized by transetherification of 3,4-dimethoxythiophene with (S)-1,2-octanediol and purified to a purity of 99.69% as described in INVENTION EXAMPLE 1. It was characterized by GC-MS and $^1$H-NMR-spectroscopy, and exhibited a specific rotation of −100° at 25° C. and 436 nm in hexane.

COMPARATIVE EXAMPLE 4

Synthesis of racemic
2-n-hexyl-2,3-dihydro-thieno[3,4-b][1,4]dioxine

Racemic 2-n-hexyl-2,3-dihydro-thieno[3,4-b][1,4]dioxine was synthesized by transetherification of 3,4-dimethoxythiophene with racemic 1,2-octanediol as described in EXAMPLE 1. It was characterized by GC-MS and $^1$H-NMR-spectroscopy, and exhibited no optical rotation.

INVENTION EXAMPLE 3

Synthesis of chiral
2-n-octyl-2,3-dihydro-thieno[3,4-b][1,4]dioxine

Chiral 2-n-octyl-2,3-dihydro-thieno[3,4-b][1,4]dioxine was synthesized by transetherification of 3,4-dimethoxythiophene with (S)-1,2-decanediol and purified to a purity of 99.24% as described in INVENTION EXAMPLE 1. It was characterized by GC-MS and $^1$H-NMR-spectroscopy, and exhibited a specific rotation of −88° at 25° C. and 436 nm in hexane.

INVENTION EXAMPLE 4

Synthesis of chiral
2-n-dodecyl-2,3-dihydro-thieno[3,4-b][1,4]dioxine

Chiral 2-n-dodecyl-2,3-dihydro-thieno[3,4-b][1,4]dioxine was synthesized by transetherification of 3,4-dimethoxythiophene with (S)-1,2-tetradecanediol and purified to a purity of 98.01% as described in INVENTION EXAMPLE 1. It was characterized by GC-MS and $^1$H-NMR-spectroscopy, and exhibited a specific rotation of −65° at 25° C. and 436 nm in hexane.

Electropolymerization of the
3,4-ethylenedioxythiophene Derivatives of
INVENTION EXAMPLE 1 to 4 and
COMPARATIVE EXAMPLES 1 to 4

Electropolymerization was performed at 25° C. using a standard three electrode cell. The working electrode was platinum, gold or indium-tin-oxide. The counter electrodes was platinum; the reference electrode was silver/0.1 M silver perchlorate in acetonitrile (0.34 V vs SCE).

Acetonitrile solutions 10 M in one of the 2-alkyl-2,3-dihydro-thieno[3,4-b][1,4]dioxine compounds of INVENTION EXAMPLE 1 to 4 and COMPARATIVE EXAMPLES 1 to 5 and 0.1 M in NaClO$_4$ were polymerized by applying a potential of 0.7–0.8 V in the cell shown in FIG. 1. A current density of 5 mA cm$^{-2}$ was used in the electropolymerization.

In-situ Electrical Conductivity Measurements of the
Electropolymerized 3,4-ethylenedioxythiophene
Derivatives of INVENTION EXAMPLE 1 to 4 and
COMPARATIVE EXAMPLES 1 to 4

Electrical conductivity measurements were carried out in the absence of monomer in the same three electrode cell in which the electropolymerization was carried out. The electrode for conductivity measurements was a two-band platinum electrode (0.3 cm×0.01 cm for each band) with an interband spacing of 20 μm, as shown in FIG. 1. The platinum electrode was coated with polymer by the passage of 80 mC, which assured the attainment of limiting resistance conditions. Electrical conductivities were measured by applying a small amplitude (typically 10 mV) DC voltage between the bands and recording the current thereby obtained. Poly(3-methylthiophene) (60 S/cm) was used as an electrical conductivity standard. The results are shown electrical conductivities observed upon electropolymerizing the 2-alkyl-2,3-dihydro-thieno[3,4-b][1,4]-dioxine compounds of INVENTION EXAMPLES 1 to 4 and COMPARATIVE EXAMPLES 1 to 4 are given in Table 3.

TABLE 3

| Monomer from Example nr | Polymer | Electrical conductivity in scm$^{-1}$ |
|---|---|---|
| Comparative 1 | electropolymerized chiral 2-methyl-2,3-dihydro-thieno-[3,4-b] [1,4]dioxine | 350 |
| Comparative 2 | electropolymerized racemic mixture of d- & l- 2-methyl-2,3-dihydro-thieno-[3,4-b] [1,4]dioxine | 350 |
| Invention 1 | electropolymerized chiral 2-n-decyl-2,3-dihydro-thieno[3,4-b] [1,4]dioxine | 1500 |
| Comparative 3 | electropolymerized racemic mixture of d- and l- 2-n-decyl-2,3-dihydro-thieno-[3,4-b] [1,4]dioxine | 550 |
| Invention 2 | electropolymerized chiral 2-n-hexyl-2,3-dihydro-thieno[3,4-b] [1,4]dioxine | 1800 |
| Comparative 4 | electropolymerized racemic mixture of d- and l- 2-n-hexyl-2,3-dihydro-thieno-[3,4-b] [1,4]dioxine | 200 |
| Invention 3 | electropolymerized chiral 2-n-octyl-2,3-dihydro-thieno[3,4-b] [1,4]dioxine | 1500 |
| Invention 4 | electropolymerized chiral 2-n-dodecyl-2,3-dihydro-thieno[3,4-b] [1,4]dioxine | 600 |

The results in Table 3 show that electropolymerized chiral 2-methyl-2,3-dihydro-thieno[3,4-b][1,4]dioxine exhibited an identical electrical conductivity to electropolymerized racemic mixture of d- and l- 2-methyl-2,3-dihydro-thieno [3,4-b][1,4]dioxine.

However, electropolymerized chiral 2-n-decyl-2,3-dihydro-thieno[3,4-b][1,4]dioxine exhibited a 2.7-fold increase in electrical conductivity over that obtained with a electropolymerized racemic mixture of d- and l- 2-n-decyl-2,3-dihydro-thieno[3,4-b][1,4]dioxine.

Furthermore, electropolymerized chiral 2-n-hexyl-2,3-dihydro-thieno[3,4-b][1,4]dioxine exhibited a 9-fold increase in electrical conductivity over that obtained with a electropolymerized racemic mixture of d- and l- 2-n-hexyl-2,3-dihydro-thieno[3,4-][1,4]dioxine.

Electropolymerized chiral 2-n-octyl-2,3-dihydro-thieno[3,4-][1,4]dioxine and chiral 2-n-dodecyl-2,3-dihydro-thieno[3,4-][1,4]dioxine exhibit electrical conductivities of 1500 and 600 S/cm respectively.

Since these measurements were carried out in an identical manner and in the same apparatus as those disclosed by Groenendaal et al. in 2001 in Synthetic Metals, volume 118(1–3), on pages 105–109, they can be directly compared with the electrical conductivity value given by Groenendaal et al. for poly(3,4-ethylenedioxy-thiophene) of 650 S cm$^{-1}$. Therefore, electropolymerized chiral 2-hexyl-2,3-dihydro-thieno[3,4-b][1,4]dioxine, chiral 2-n-octyl-2,3-dihydro-thieno[3,4-b][1,4]dioxine and chiral 2-n-decyl-2,3-dihydro-thieno[3,4-b][1,4]dioxine exhibited a 2.8-fold, 2.3-fold and 2.3-fold increase respectively in electrical conductivity over that obtained for poly(3,4-ethylenedioxythiophene).

Such in-situ electrical conductivity measurements are a relatively new and very interesting tool to measure electrical conductivities of electrochemically polymerized conducting polymer films as a function of their oxidation state. The technique has a number of advantages compared to standard electrical conductivity measurements (2- or 4-point probe): only small amounts of monomer are required (15–50 mg), all monomers are polymerized under exactly the same conditions, the measurements are very fast, the electrical conductivity values obtained are hardly influenced by external factors such as humidity, air, etc., since the measurements are performed under inert conditions, and in addition to the maximum value of the electrical conductivity, information is also obtained about the influence of the oxidation state on the electrical conductivity.

The present invention may include any feature or combination of features disclosed herein either implicitly or explicitly or any generalisation thereof irrespective of whether it relates to the presently claimed invention. In view of the foregoing description it will be evident to a person skilled in the art that various modifications may be made within the scope of the invention.

What is claimed is:

1. A composition consisting essentially of a thiophene compound represented by formula (I):

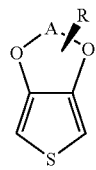

(I)

in which:

A represents a C2–C5 alkylene bridge; R represents a stereoselectively substituted, linear or branched C2–C24 alkyl, C3–C18 cycloalkyl, C1–C18 alkoxy or polyethyleneoxide group, optionally substituted with at least one substituent selected from the group consisting of an alcohol, amide, ether, ester and sulfonate group; or an optionally substituted aryl group having at least one chiral centre substituted at said C2–C5 alkylene bridge.

2. The composition according to claim 1, wherein said group R is a C4–C20 alkyl group.

3. The composition according to claim 1, wherein said group R is a C6–C18 alkyl group.

4. A poly(3,4-alkylenedioxy-thiophene) prepared from compounds consisting essentially of thiophene compounds represented by formula (I):

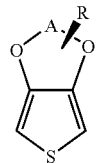

(I)

in which:

A represents a C2–C5 alkylene bridge; R represents a stereoselectively substituted, linear or branched C2–C24 alkyl, C3–C18 cycloalkyl, C1–C18 alkoxy or polyethyleneoxide group, optionally substituted with at least one substituent selected from the group consisting of an alcohol, amide, ether, ester and sulfonate group; or an optionally substituted aryl group having at least one chiral centre substituted at said C2–C5 alkylene bridge.

5. The poly(3,4-alkylenedioxy-thiophene) according to claim 4, wherein said poly(3,4-alkylenedioxy-thiophene) is poly{chiral 2-n-hexyl-2,3-dihydro-thieno[3,4-b][1,4]dioxine}.

6. The poly(3,4-alkylenedioxy-thiophene) according to claim 4, wherein said poly(3,4-alkylenedioxy-thiophene) is poly{chiral 2-n-octyl-2,3-dihydro-thieno[3,4-b][1,4]dioxine}.

7. The poly(3,4-alkylenedioxy-thiophene) according to claim 4, wherein said poly(3,4-alkylenedioxy-thiophene) is poly{chiral 2-n-decyl-2,3-dihydro-thieno[3,4-b][1,4]dioxine}.

8. A printable paste comprising a poly(3,4-alkylenedioxy-thiophene) prepared from compounds consisting essentially of thiophene compounds represented by formula (I):

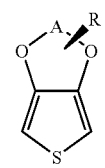

(I)

in which:

A represents a C2–C5 alkylene bridge; R represents a stereoselectively substituted, linear or branched C2–C24 alkyl, C3–C18 cycloalkyl, C1–C18 alkoxy or polyethyleneoxide group, optionally substituted with at least one substituent selected from the group consisting of an alcohol, amide, ether, ester and sulfonate group; or an optionally substituted aryl group having at least one chiral centre substituted at said C2–C5 alkylene bridge.

9. An electroconductive layer comprising a poly(3,4-alkylenedioxy-thiophene) prepared from compounds consisting essentially of thiophene compounds represented by formula (I):

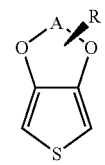

(I)

in which:

A represents a C2–C5 alkylene bridge; R represents a stereoselectively substituted, linear or branched C2–C24 alkyl, C3–C18 cycloalkyl, C1–C18 alkoxy or polyethyleneoxide group, optionally substituted with at least one substituent selected from the group consisting of an alcohol, amide, ether, ester and sulfonate group; or an optionally substituted aryl group having at least one chiral centre substituted at said C2–C5 alkylene bridge.

10. An electroconductive layer comprising a poly(3,4-alkylenedioxy-thiophene) prepared from compounds consisting essentially of thiophene compounds represented by formula (I):

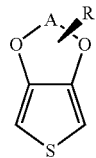

in which:

A represents a C2–C5 alkylene bridge; R represents a stereoselectively substituted, linear or branched C2–C24 alkyl, C3–C18 cycloalkyl, C1–C18 alkoxy or polyethyleneoxide group, optionally substituted with at least one substituent selected from the group consisting of an alcohol, amide, ether, ester and sulfonate group; or an optionally substituted aryl group having at least one chiral centre substituted at said C2–C5 alkylene bridge.

11. The printable paste of claim 8, wherein said poly(3,4-alkylenedioxy-thiophene) is poly{chiral 2-n-hexyl-2,3-dihydro-thieno[3,4-b][1,4]dioxine}.

12. The printable paste of claim 8, wherein said poly(3,4-alkylenedioxy-thiophene) is poly{chiral 2-n-octyl-2,3-dihydro-thieno[3,4-b][1,4]dioxine}.

13. The printable paste of claim 8, wherein said poly(3,4-alkylenedioxy-thiophene) is poly{chiral 2-n-decyl-2,3-dihydro-thieno[3,4-b][1,4]dioxine}.

14. The electroconductive layer of claim 9, wherein said poly(3,4-alkylenedioxy-thiophene) is poly{chiral 2-n-hexyl-2,3-dihydro-thieno[3,4-b][1,4]dioxine}.

15. The electroconductive layer of claim 9, wherein said poly(3,4-alkylenedioxy-thiophene) is poly{chiral 2-n-octyl-2,3-dihydro-thieno[3,4-b][1,4]dioxine}.

16. The electroconductive layer of claim 9, wherein said poly(3,4-alkylenedioxy-thiophene) is poly{chiral 2-n-decyl-2,3-dihydro-thieno[3,4-b][1,4]dioxine}.

17. The antistatic layer of claim 10, wherein said poly(3,4-alkylenedioxy-thiophene) is poly{chiral 2-n-hexyl-2,3-dihydro-thieno[3,4-b][1,4]dioxine}.

18. The antistatic layer of claim 10, wherein said poly(3,4-alkylenedioxy-thiophene) is poly{chiral 2-n-octyl-2,3-dihydro-thieno[3,4-b][1,4]dioxine}.

19. The antistatic layer of claim 10, wherein said poly(3,4-alkylenedioxy-thiophene) is poly{chiral 2-n-decyl-2,3-dihydro-thieno[3,4-b][1,4]dioxine}.

20. A polymer prepared from compounds consisting essentially of a thiophene compound represented by formula (I):

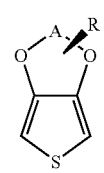

in which:

A represents a C2–C5 alkylene bridge; R represents a stereoselectively substituted, linear or branched C2–C24 alkyl, C3–C18 cycloalkyl, C1–C18 alkoxy or polyethyleneoxide group, optionally substituted with at least one substituent selected from the group consisting of an alcohol, amide, ether, ester and sulfonate group; or an optionally substituted aryl group having at least one chiral centre substituted at said C2–C5 alkylene bridge, and a polymerizable heterocyclic compound other than a 3,4-alkylenedioxythiophene.

21. The polymer of claim 20, wherein the polymerizable heterocyclic compound is pyrrole.

* * * * *